United States Patent [19]

Kukolja et al.

[11] 4,394,313

[45] Jul. 19, 1983

[54] SYMMETRICAL AZETIDINONE ALDEHYDE DISULFIDES AND PROCESS

[75] Inventors: Stjepan Kukolja, Carmel; Janice L. Pfeil, Indianapolis, both of Ind.

[73] Assignee: Eli Lilly and Company, Indianapolis, Ind.

[21] Appl. No.: 264,996

[22] Filed: May 18, 1981

Related U.S. Application Data

[62] Division of Ser. No. 138,023, Apr. 7, 1980, Pat. No. 4,293,495.

[51] Int. Cl.$^3$ ............... C07D 403/12; C07D 487/04; C07D 403/14
[52] U.S. Cl. ................................. 260/245.4
[58] Field of Search ....................... 260/245.4

[56] References Cited

U.S. PATENT DOCUMENTS 4,302,391 11/1981 Kukolja ..................... 260/245.4

OTHER PUBLICATIONS

Pfeil et al., J. Organic Chem. 46, 827 (1981).
Gorden et al., Chem. Abs. 88, 121082d (1977).
Paquette et al., Syn. Comm. 6, 575 (1976).

*Primary Examiner*—Mark L. Berch
*Attorney, Agent, or Firm*—Paul C. Steinhardt; William B. Scanlon; Arthur R. Whale

[57] ABSTRACT

4R, 4′R bis [1-(2-N-3-methyl-4-al-Z-but-2-ene-oate)-2-oxo-3S-acylamino azetidine]disulfide compounds are prepared by reacting the corresponding 7α-acylamino-2α-alkoxy-3-methyl-3-cephem-4-carboxylates first with an N-chloro halogenating agent, e.g., N-chlorosuccinimide, then with an aqueous suspension of mercury dichloride and cadmium carbonate. The disulfide compounds produced in this invention are intermediates in the synthesis of the biologically active 7β-acyl-amino-7α-alkoxy-3-methyl 1-oxa β-lactam antibiotic compounds.

15 Claims, No Drawings

SYMMETRICAL AZETIDINONE ALDEHYDE DISULFIDES AND PROCESS

This application is a division, of application Ser. No. 138,023, filed Apr. 7, 1980 now U.S. Pat. No. 4,293,495.

BACKGROUND OF THE INVENTION 1-oxa-$\beta$-lactam compounds, which possess the following general structure:

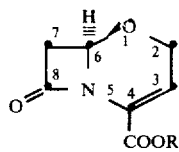

have recently been the subject of extensive research efforts due to their antibacterial activity. Specifically, there have been recent reports of syntheses of 1-oxa $\beta$-lactam compounds substituted with methyl at the C-3 postion. For example, Naylor et al. in "Recent Advances in the Chemistry of $\beta$-Lactam Antibiotics" (J. Elks, ed.), The Chemical Society, London, 1977, p. 204, reported a synthesis of 1-oxacephalexin. Similarly, Narisada et al., *Heterocycles*, 7, 839 (1977), were able to prepare several 3-methyl 1-oxa $\beta$-lactam compounds which exhibited antibacterial activity from four to eight times greater than the corresponding cephalosporins. The present application describes and claims novel intermediates which can be employed in the synthesis of the aforementioned biologically active 7$\beta$-acylamino-7$\alpha$-alkoxy-3-methyl 1-oxa $\beta$-lactam compounds. The process for the preparation of such intermediates is an alternate aspect of the present invention.

SUMMARY OF THE INVENTION

This invention is directed to 4R,4'R bis [1-(2-N-3-methyl-4-al-Z-but-2-ene-oate)-2-oxo-3S-acylamino azetidinone]disulfide compounds (referred to herein as symmetrical azetidinone aldehyde disulfide compounds), and to a method for their preparation. According to the process of this invention, a 7$\alpha$-acylamino-2$\alpha$-alkoxy-3-methyl-3-cephem-4-carboxylate compound is first reacted in a chlorinated hydrocarbon solvent with between 1 to 1.3 moles of an N-chloro halogenating reagent at temperatures between about $-10°$ and about 30° C. The reaction solution so obtained is then added to an aqueous suspension of from about 2 to about 4 moles of mercury dichloride and from about 5 to about 7 moles of cadmium carbonate at a temperature of about 0° to about 30° C. The N-chloro halogenating agents which can be used include the N-chloro ureas, imides, amides, urethanes, sulfonamides, sulfimides, imides, hydantoins and isocyanuric acids, with the preferred agents being N-chlorosuccinimide and N-chlorophthalimide.

The novel disulfide compounds produced by the process of the invention are useful as intermediates in the synthesis of a particular class of 1-oxa $\beta$-lactam antibiotics. Specifically, a symmetrical azetidinone aldehyde disulfide compound of the invention is first reduced to the corresponding alcohol, and then cyclized to provide the desired 1-oxa $\beta$-lactam nucleus. This nucleus is then $\alpha$-methoxylated at the C-7 position and the carboxylic acid protecting group is subsequently removed to give the biologically active 7$\beta$-acylamino-7$\alpha$-alkoxy-3-methyl-1-oxa $\beta$-lactam acid compounds, a class of 1-oxa $\beta$-lactam antibiotic compounds.

DETAILED DESCRIPTION OF THE INVENTION

This invention is directed to compounds of the following general formula I:

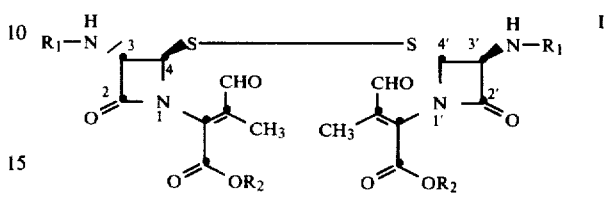

and the process for their preparation. These compounds are referred to in this application, for convenience sake, as "symmetrical azetidinone aldehyde disulfide" compounds. In the above term, "symmetrical" refers to the presence of identically substituted azetidinone moieties bonded to either end of the disulfide group and "aldehyde" calls attention to the aldehyde group on the side chain attached to the azetidinone nitrogen, emphasizing that this aldehyde group is not the alcohol function required for cyclization of the molecule to a 1-oxa $\beta$-lactam compound.

When the reduction of the aldehyde group to the alcohol group is accomplished, the resultant compound is referred to as the "symmetrical azetidinone alcohol disulfide" compound.

The 1-oxa $\beta$-lactam antibiotics obtained from the azetidinone disulfides of the invention possess the following bicyclic ring system:

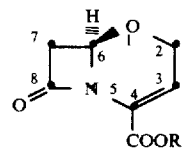

wherein R can be hydrogen or a conventional carboxylic acid protecting group.

In the formulas contained in this application, the mark "▬◀" means $\beta$-configuration and the dotted line "∥∥∥∥∥∥" means $\alpha$-configuration.

The symmetrical azetidinone aldehyde disulfide compounds of this invention are represented by the following general formula I

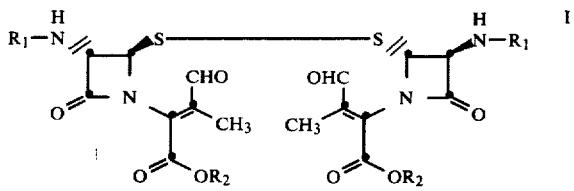

wherein $R_1$ is an acyl group of the formula

wherein R' is (a) $C_1$-$C_7$ alkyl, cyanomethyl, $C_1$-$C_6$ haloalkyl, 4-protected amino-4-protected carboxybutyl; or (b) $C_1$-$C_6$ alkoxy, phenoxy, banzyloxy or 4-methoxybenzyloxy; or (c) the group —R" wherein R" is phenyl or substituted phenyl, wherein the substituents are 1 or 2 halogens, protected hydroxy, cyano, trifluoromethyl, $C_1$-$C_4$ alkyl, $C_1$-$C_4$ alkoxy, protected carboxy, protected carboxymethyl, protected hydroxymethyl or protected aminomethyl; or (d) an arylalkyl group of the formula R"—(O)$_m$—CH$_2$— wherein R" is as defined above, and m is 0 or 1; or (e) a substituted arylalkyl group of the formula

wherein R'" is R" as defined above, 2-thienyl, 3-thienyl, 2-furyl or 3-furyl; W is protected hydroxy, protected carboxy, protected amino, or (f) a heteroarylmethyl group of the formula R""—CH$_2$— wherein R"" is 2-thienyl, 3-thienyl, 2-furyl, 3-furyl, 2-thiazolyl, 5-tetrazolyl, 1-tetrazolyl; and, $R_2$ is a carboxy protecting group.

In the following specification, the protecting group designation is omitted for simplicity in nomenclature, but it is understood that in the description of the process of this invention, each carboxy, hydroxy or amino group is a protected group.

In the foregoing definitions of the compounds of this invention, the term "$C_1$-$C_7$ alkyl" refers to methyl, ethyl, n-propyl, n-butyl, isobutyl, pentyl, n-hexyl, cyclohexyl, n-heptyl and like aliphatic hydrocarbon chains.

The term "$C_1$-$C_6$ haloalkyl" refers to chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

The term, "protected amino" as employed in the above definition has reference to an amino group substituted with one of the commonly employed amino blocking groups such as the tert-butoxycarbonyl group (t-BOC), the benzyloxycarbonyl group, the 4-methoxybenzyloxycarbonyl group, the 2,2,2-trichloroethoxycarbonyl group, the trimethylsilyl group, and like amino protecting groups. The nature of such amino protecting groups is not critical so long as the protected amino functionality is stable under the reaction conditions of the reduction step described hereinafter.

The term "protected hydroxy" has reference to any group stable under the reaction conditions of the subsequent reduction step in this synthesis of the 1-oxa β-lactam compounds, but readily cleavable thereafter. Such groups include the formyloxy group, the chloroacetoxy group, the benzhydryloxy group, the trityloxy group, the trimethylsilyl group, and the like.

The term "protected carboxy" or "carboxy protecting group" has reference to a carboxy group which has been esterified with one of the commonly used carboxylic acid protecting ester groups employed to block or protect the carboxylic acid functionality while reactions involving other functional sites of the compound are carried out. Such protected carboxy groups are noted for their ease of cleavage by hydrolytic methods to the corresponding carboxylic acid. Examples of carboxylic acid protecting groups include tert-butyl, 4-methoxybenzyl, diphenylmethyl, benzyl, 2,4,6-trimethoxybenzyl, trityl, 4-methoxytrityl, 4,4'-dimethoxytrityl, 4,4',4"-trimethoxytrityl and like ester forming moieties. The nature of such ester forming groups is not critical so long as the ester formed therewith is stable under the reaction conditions of the reduction step described hereinafter. Preferred carboxylic acid protecting groups are benzyl, diphenylmethyl, tert-butyl, p-methoxybenzyl, 2,4,6-trimethylbenzyl, trityl, 4-methoxytrityl, 4,4'-dimethoxytrityl, and 4,4',4"-trimethoxytrityl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention, such as those described in J. F. W. McOmie, "Protective Groups in Organic Chemistry," Plenum Press, 1973, will be recognized as suitable. Thus, there is no novelty or inventiveness asserted with regard to the "protecting groups" alluded to in this specification.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a cyanophenyl group, for example 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R" represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

Illustrative of the acyl groups,

wherein R' is $C_1$-$C_7$ alkyl or $C_1$-$C_6$ haloalkyl are acetyl, propionyl, butyryl, hexanoyl, chloroacetyl, bromoacetyl and the like.

Representative of the acyl groups

when R' is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, and 3-aminobenzoyl.

Illustrative of the acyl groups

when R' is a group of the formula R"—(O)$_m$—CH$_2$—, m is 0 and R" is phenyl or substituted phenyl, are phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when R' is a substituted arylalkyl group of the formula

are the carboxy substituted aryl groups such as the 2-carboxyl-2-phenylacetyl group of the formula

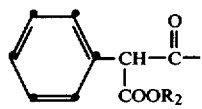

and similar groups wherein the phenyl ring is substituted, for example, 2-carboxy-2-(4-chlorophenyl)acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-carboxymethylphenyl)acetyl, 2-carboxy-2-(4-hydroxymethylphenyl)acetyl and like groups.

Representative of the acyl groups when R' is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4(1-amino-1-methyl)phenyl)acetyl, 2-hydroxy-2-(3-thienyl)-acetyl.

When R' is an amino substituted arylalkyl group, acyl groups represented thereby include 2-amino-2-phenylacetyl, 2-amino-2-(4-cyanophenyl)acetyl, 2-amino-2-(4-hydroxyphenyl)acetyl, and like groups.

Representative of the acyl group

when R' is a heteroarylmethyl group of the formula R""—CH$_2$— are 2-thienylacetyl, 3-thienylacetyl, 2-furylacetyl, 2-thiazolylacetyl, 1-tetrazolylacetyl, a 5-tetrazolylacetyl and the like.

The symmetrical azetidinone aldehyde disulfides of the present invention are prepared by reacting a 7α-acylamino-2α-alkoxy-3-methyl-3-cephem-4-carboxylate with an N-chloro halogenating reagent and then with an aqueous suspension of mercury dichloride and cadmium carbonate as illustrated in the following general reaction scheme.

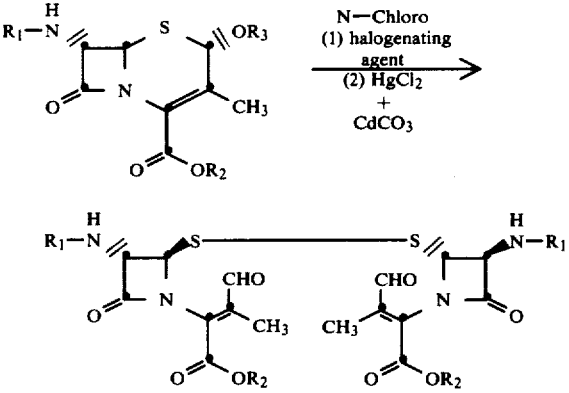

In the above general reaction scheme R$_1$ and R$_2$ are as described for general formula I, R$_3$ is methyl, ethyl or isopropyl, and "N-chloro halogenating agent" is a compound of the general formula:

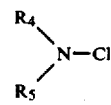

where R$_4$ is hydrogen, chloro, C$_1$-C$_3$ alkyl, cyclohexyl, phenyl, or phenyl substituted with chloro, bromo, methyl, or nitro, and R$_5$ is R$_6$—X— in which R$_6$ is C$_1$-C$_3$ alkyl, cyclohexyl, phenyl, or phenyl substituted with chloro, bromo, methyl, or nitro, and X is

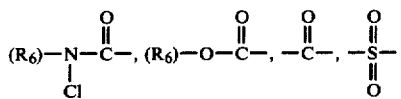

or R$_4$ and R$_5$ taken together with the nitrogen to which they are bonded define a heterocyclic structure of the formula

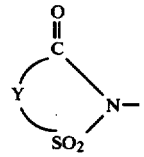

in which Y is o-phenylene, or —(CH$_2$)$_n$— in which n is 2 or 3; or a structure of the formula

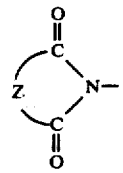

in which Z is Y as hereinbefore defined or a group of the formula

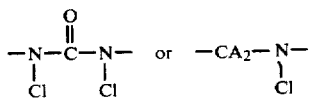

in which A is hydrogen or methyl.

The process of this invention is carried out by reacting a 7α-acylamino-2α-alkoxy-3-methyl-3-cephem-4-carboxylic acid ester in a chlorinated hydrocarbon solvent with at least about 1 mole of an N-chloro halogenating reagent per mole of cephalosporin compound. When the halogenation step is completed, the reaction mixture is added to an agitated aqueous suspension of at least about 2 moles of mercury dichloride and at least about 5 moles of cadmium carbonate per mole of cephalosporin substrate to effect the disulfide formation step.

Both the halogenation step and the disulfide formation step of this process can be performed at a temperature between about 0° C. and about 30° C. Preferably the reaction is carried out at temperatures between about 0° C. and about 15° C.

Although at least about 1 molar equivalent of the N-chloro halogenating reagent is required for complete conversion, it is preferable to employ between about 1 and about 1.3 moles of the N-chloro halogenating reagent per mole of the cephalosporin substrate. Although at least about 2 molar equivalents of mercury dichloride and at least about 5 molar equivalents of cadmium carbonate are required for complete disulfide formation, it is preferable to use between about 3 and about 3.5 moles of mercury dichloride and between about 6 and about 6.5 moles of cadmium carbonate per mole of the cephalosporin starting material.

As mentioned above, the halogenation step of this process is carried out in a halogenated hydrocarbon solvent. The term "halogenated hydrocarbon solvent" includes solvents in which the cephalosporin substrate and the N-chloro halogenating agent are at least partially soluble. Chlorinated hydrocarbon solvents which can be employed include methylene chloride, chloroform, dichloroethane, trichloroethane, chlorobenzene, carbon tetrachloride, 1,1-dibromo-2-chloroethane and the like. Methylene chloride is the preferred solvent in this process.

Any of a wide variety of N-chloro halogenating agents are suitable for use in the present process. These N-chloro compounds include N-chlorinated (a) ureas (b) amides (c) urethanes (d) sulfonamides, (e) sulfimides, (f) imides, (g) hydantoins, and (h) isocyanuric acids.

The N-chloro ureas which can be employed in this invention generally have the formula

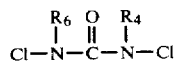

in which R₄ is hydrogen, chloro, C₁-C₃ alkyl, cyclohexyl, phenyl, or phenyl substituted with chloro, bromo, methyl, or nitro, and R₆ is C₁-C₃ alkyl, cyclohexyl, phenyl, or phenyl substituted with chloro, bromo, methyl, or nitro.

Illustrative of these ureas are
N,N'-dichloro-N-methylurea;
N,N'-dichloro-N-ethyl-N'-cyclohexylurea;
N,N'-dichloro-N-phenylurea;
N,N'-dichloro-N,N'-diphenylurea;
N,N'-dichloro-N-(p-tolyl)urea;
N,N'-dichloro-N-(m-chlorophenyl)-N'-methylurea;
N,N'-dichloro-N,N'-dicyclohexylurea;
N,N'-dichloro-N-isopropyl-N'-(p-tolyl)urea;
N,N'-dichloro-N-phenyl-N'-propylurea;
N,N'-dichloro-N-cyclohexyl-N'-(p-nitrophenyl)urea;
and the like.

The N-chloro amides which can be employed in this invention generally have the formula

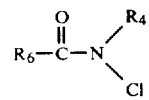

in which R₄ and R₆ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)-butyramide, N-chloro-2,4-trichloroacetamide, and the like.

The N-chloro urethanes which can be used in halogenating the cephalosporin starting materials in accordance with this invention have the general formula

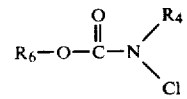

in which R₄ and R₆ are as hereinbefore defined.

Illustrative of these urethanes are methyl N,N-dichlorocarbamate, ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorophenyl N-methyl-N-chlorocarbamate, cyclohexyl N-cyclohexyl-chlorocarbamate, isopropyl N-p-tolyl-N-chlorocarbamate, phenyl N-propyl-N-chlorocarabmate, cyclohexyl N-p-nitrophenyl-N-chlorocarbamate, and the like.

The N-chloro sulfonamides which can be used in halogenating the cephalosporin compounds in accordance with this invention have the general formula

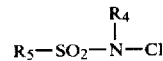

in which R₄ and R₅ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorobenzenesulfonamide, N-methyl-N-chloro-p-toluenesulfonamide, N-cyclohexyl-N- chlorocyclohexanesulfonamide, N-p-tolyl-N-chloroisopropanesulfonamide, N-propyl-N-chlorobenzenesulfonamide, N-p-nitrophenyl-N-chlorocyclohexanesulfonamide, and the like.

A further type of N-chloro halogenating agent which can be employed in the preparation of the present symmetrical azetidinone aldehyde disulfide compounds is a sulfimide of the formula

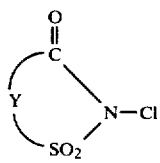

in which Y is o-phenylene, —CH$_2$—CH$_2$—, or —CH$_2$—CH$_2$—CH$_2$—. These compounds include o-sulfobenzoic N-chloroimide, β-sulfopropionic N-chloroimide, and γ-sulfobutyric N-chloroimide.

Also useful as N-chloro halogenating agents in the preparation of symmetrical disulfide compounds in accordance with this invention are N-chloroimides of the formula

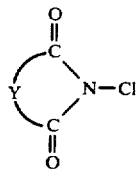

in which Y is o-phenylene, —CH$_2$—CH$_2$—, or —CH$_2$—CH$_2$—CH$_2$—. These compounds include N-chlorophthalimide, N-chlorosuccinimide, and N-chloroglutarimide.

N,N'-Dichlorohydantoins can also be employed as halogenating agents in preparing the disulfide compounds of this invention. These hydantoins have the formula

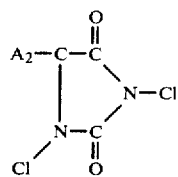

in which A is hydrogen or methyl, and include 1,3-dichlorohydantoin, 1,3-dichloro-5-methylhydantoin, and 1,3-dichloro-5,5-dimethylhydantoin.

Another type of halogenating agent which can be employed in the present process are the isocyanuric acids, which includes N,N',N''-trichloroisocyanuric acid of the formula

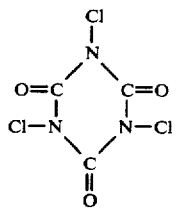

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., *Journal of Organic Chemistry*, 39, (1974) pp. 3136-3138; Theilacker et al., *Liebigs Annalen der Chemie*, 703, (1967) pp. 34-36; and Houben-Weyl, *Methoden der Organischen Chemie*, Volume V/3, pp. 796-810.

N-Chloro halogenating agents which are highly preferred for use in the process of this invention are N-chloro imides, and particularly N-chlorosuccinimide or N-chlorophthalimide.

In carrying out the process of the invention, a 7α-acylamino-2α-alkoxy-3-methyl-3-cephem-4-carboxylate and an N-chloro halogenating reagent are combined in a chlorinated hydrocarbon. This reaction mixture is agitated, for example, with stirring, until the halogenation is complete. The halogenation reaction mixture is subsequently added to a rapidly stirred aqueous suspension of mercury dichloride and cadmium carbonate. The disulfide formation reaction is typically complete in 0.5 hour.

For example, a 7α-acylamino-2α-alkoxy-3-methyl-3-cephem-4-carboxylate substrate compound is combined in a one to one molar ratio with N-chlorosuccinimide in methylene chloride at 0° C. This solution is agitated with stirring for 15 minutes, then added to a rapidly agitated aqueous suspension of mercury dichloride and cadmium carbonate for 0.5 hour at ambient temperature. The mercury dichloride and cadmium carbonate are present in a 3 to 1 and 6 to 1 molar ratio, respectively, to the substrate 7α-acylamino-2α-alkoxy-3-methyl-3-cephem-4-carboxylate substrate compound.

A preferred group of 7α-acylamino-2α-alkoxy-3-methyl-3-cephem-4-carboxylates which can be converted to the symmetrical azetidinone aldehyde disulfide compounds according to the process of this invention are represented by the following general formula II:

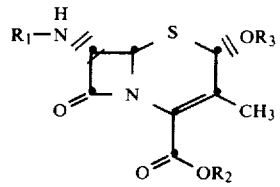

wherein R$_1$ is an acyl group of the formula

wherein R' is
(a) C$_1$-C$_7$ alkyl, or cyanomethyl
(b) C$_1$-C$_6$ alkoxy
(c) an arylalkyl group of the formula

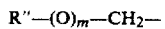

wherein R'' is phenyl or substituted phenyl wherein the substituents are 1 or 2 halogens, hydroxy, cyano, trifluoromethyl, C$_1$-C$_4$ alkyl, C$_1$-C$_4$ alkoxy, carboxy, carboxymethyl, hydroxymethyl or aminomethyl; and m is 0 or 1;

(d) 2-thienylmethyl, 3-thienylmethyl, 2-furylmethyl, 3-furylmethyl, 2-thiazolylmethyl, 5-tetrazolylmethyl, 1-tetrazolylmethyl;

(e) 1-hydroxy-1-phenylmethyl, 1-amino-1-phenylmethyl, 1-amino-1-(4-hydroxyphenyl)methyl;

$R_3$ is methyl, ethyl or isopropoxy; and $R_2$ is benzyl, tert-butyl or 4-methoxybenzyl.

Illustrative compounds described above which can be employed as starting materials in the process of this invention include the following 7α-acylamino-2α-alkoxy-3-methyl-3-cephem-4-carboxylates:

benzyl 7α-octamido-2α-methoxy-3-methyl-3-cephem-4-carboxylate, benzyl 7α-cyanoacetamido-2α-methoxy-3-methyl-3-cephem-4-carboxylate, benzyl 7α-[2-(2-thienyl)acetamido]-2α-methoxy-3-methyl-3-cephem-4-carboxylate, benzyl 7α-phenylacetamido-2α-methoxy-3-methyl-3-cephem-4-carboxylate, tert-butyl 7α-[2-(2-furyl)acetamido]-2α-methoxy-3-methyl-3-cephem-4-carboxylate, p-methoxybenzyl 7α-benzamido-2α-methoxy-3-methyl-3-cephem-4-carboxylate, p-methoxybenzyl 7α-benzamido-2α-isopropoxy-3-methyl-3-cephem-4-carboxylate, benzyl 7α-phenoxyacetamido-2α-methoxy-3-methyl-3-cephem-4-carboxylate, benzyl 7α-phenoxyacetamido-2α-isopropoxy-3-methyl-3-cephem-4-carboxylate, p-methoxybenzyl 7α-(2-tert-butoxycarbonylamino-2-phenylacetamido)-2α-methoxy-3-methyl-3-cephem-4-carboxylate, benzyl 7α-(2-(tert-butoxycarbonylamino)-2-(4-benzylcarbonatophenyl)acetamido)-2α-methoxy-3-methyl-3-cephem-4-carboxylate, benzyl 7α-(2-(1-tetrazolyl)acetamido)-2α-methoxy-3-methyl-3-cephem-4-carboxylate, tert-butyl 7α-(2-(2-thiazolyl)acetamido)-2α-methoxy-3-methyl-3-cephem-4-carboxylate, benzyl 7α-(2-benzylcarbonato-2-phenylacetamido)-2α-methoxy-3-methyl-3-cephem-4-carboxylate, benzyl 7α-(2-(2-thienyl)acetamido)-2α-methoxy-3-methyl-3-cephem-4-carboxylate, and benzyl 7α-(2-carbobenzyloxy-2-phenylacetamido)-2α-methoxy-3-methyl-3-cephem-4-carboxylate.

More preferred 7α-acylamino-2α-alkoxy-3-methyl-3-cephem-4-carboxylate which can be used as substrates in the process of this invention are represented by the above structural formula II wherein (a) $R_1$ is an acyl group of the formula

wherein $R_7$ is an arylalkyl group of the formula

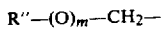

wherein R" is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; m is 0 or 1, (b) $R_3$ is methyl, (c) and $R_2$ is benzyl, 4-methoxybenzyl, or tert-butyl.

Some examples of these compounds include:

benzyl 7α-phenylacetamido-2α-methoxy-3-methyl-3-cephem-4-carboxylate, p-methoxybenzyl 7α-(2-phenoxyacetamido)-2α-methoxy-3-methyl-3-cephem-4-carboxylate, benzyl 7α-(4-chlorophenylacetamido)-2α-methoxy-3-methyl-3-cephem-4-carboxylate, benzyl 7α-(2-chlorophenylacetamido)-2α-methoxy-3-methyl-3-cephem-4-carboxylate, benzyl 7α-(2-(4-trifluoromethylphenyl)acetamido)-2α-methoxy-3-methyl-3-cephem-4-carboxylate, benzyl 7α-(2-(4-benzylcarbonatophenyl)acetamido)-2α-methoxy-3-methyl-3-cephem-4-carboxylate, p-methoxybenzyl 7α-(2-(2-(p-methoxybenzyloxy)carbonylphenyl)acetamido)-2α-methoxy-3-methyl-3-cephem-4-carboxylate, benzyl 7α-(2-(p-methoxyphenyl)acetamido)-2α-methoxy-3-methyl-3-cephem-4-carboxylate, benzyl 7α-(2-(p-methylphenyl)acetamido)-2α-methoxy-3-methyl-3-cephem-4-carboxylate, benzyl 7α-(2-(4-benzyloxycarbonylphenylacetamido)-2α-methoxy-3-methyl-3-cephem-4-carboxylate, tert-butyl 7α-(2-(4-benzylcarbonatomethylphenyl)acetamido)-2α-methoxy-3-methyl-3-cephem-4-carboxylate, p-methoxybenzyl 7α-(2-(4-benzyloxycarbonylmethylphenyl)acetamido)-2α-methoxy-3-methyl-3-cephem-4-carboxylate, benzyl 7α-(2-(4-tert-butoxycarbonylaminomethylphenyl)acetamido)-2α-methoxy-3-methyl-3-cephem-4-carboxylate, and tert-butyl 7α-(2-(4-cyanophenyl)acetamido)-2α-methoxy-3-methyl-3-cephem-4-carboxylate.

Preferred compounds of this invention are represented by the following general formula I

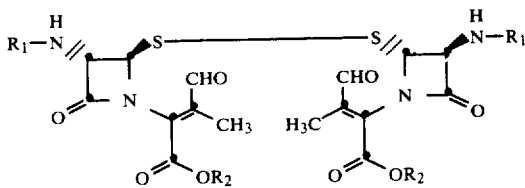

wherein $R_1$ is an acyl group of the formula

wherein R' is (a) $C_1$–$C_7$ alkyl, cyanomethyl;

(b) $C_1$–$C_6$ alkoxy (c) benzyl, phenoxymethyl, p-methoxyphenylmethyl, (d) 2-thienylmethyl, 3-thienylmethyl, 2-furylmethyl, 3-furylmethyl, 2-thiazolylmethyl, 5-tetrazolylmethyl, 1-tetrazolylmethyl;

(e) 1-protected hydroxy-1-phenylmethyl, 1-protected amino-1-phenylmethyl, 1-protected amino-1-(4-protected hydroxyphenyl)methyl, and $R_2$ is benzyl, tert-butyl or p-methoxybenzyl.

Illustrative of the preferred compounds described above of this invention include the following symmetrical azetidinone aldehyde disulfide compounds:

4R,4'R bis[1-(benzyl 2-N-3-methyl-4-al-Z-but-2-eneoate)-2-oxo-3S-phenylacetamido azetidine]-disulfide, 4R,4'R bis[1-(p-methoxybenzyl 2-N-3-methyl-4-al-Z-but-2-ene-oate)-2-oxo-3S-(2-(2-thienyl-)acetamido)azetidine]disulfide, 4R,4'R bis[1-(tert-butyl 2-N-3-methyl-4-al-Z-but-2-ene-oate)-2-oxo-3S-(2-(2-thiazolyl-)acetamido)azetidine]disulfide, 4R,4'R bis[1-(benzyl 2-N-3-methyl-4-al-Z-but-2-ene-oate)-2-oxo-3α-(2-(1-tetrazolyl-)acetamido)azetidine]disulfide, 4R,4'R bis[1-(p-methoxybenzyl 2-N-3-methyl-4-al-Z-but-2-ene-oate)-2-oxo-3S-phenoxyacetamido azetidine]disulfide, 4R,4'R bis[1-(tert-butyl 2-N-3-methyl-4-al-Z-but-2-ene-oate)-2-oxo-3S-(2-(2-furyl-)acetamido)azetidine]disulfide, 4R,4'R bis[1-(benzyl 2-N-3-methyl-4-al-Z-but-2-ene-oate)-2-oxo-3S-cyanoacetamido azetidine]disulfide, 4R,4'R bis[1-(p-methoxybenzyl 2-N-3-methyl-4-al-Z-but-2-ene-oate)-2-oxo-3S-(2-benzylcarbonato-2-phenylacetamido azetidine]disulfide, 4R,4'R bis[1-(tert-butyl 2-N-3-methyl-4-al-Z-but-2-ene-oate)-2-oxo-3S-(2-tert-butoxycarbonylamino-2-phenylacetamido)azetidine]disulfide, 4R,4'R bis[1-(benzyl 2-N-3-methyl-4-al-Z-but-2-ene-oate)-2-oxo-3S-(2-(tert-butoxycarbonylamino)-2-(4-benzylcarbonatophenyl)acetamido)azetidine]disulfide, 4R,4'R bis[1-(benzyl 2-N-3-methyl-4-al-Z-but-2-ene-oate)-2-oxo-3S-(2-benzyloxycarbonyl-2-phenylacetamido)azetidine]disulfide.

More preferred compounds of this invention are again represented by the following general formula I

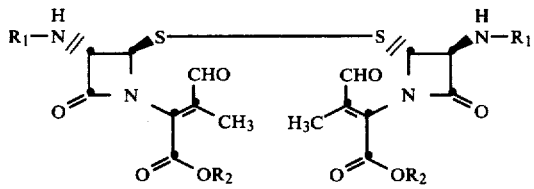

wherein R₁ is an acyl group of the formula

wherein R' is of the formula

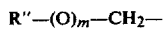

wherein R" is phenyl or substituted phenyl wherein the substituents are 1 or 2 halogens, protected hydroxy, cyano, trifluoromethyl, C₁-C₄ alkyl, C₁-C₄ alkoxy, protected carboxy, protected carboxymethyl, protected hydroxymethyl or protected aminomethyl; and m is 0 or 1 and R₂ is benzyl, tert-butyl or p-methoxybenzyl.

Illustrative of the more preferred compounds described above include the following symmetrical azetidinone aldehyde disulfide compounds:

4R,4'R bis[1-(benzyl 2-N-3-methyl-4-al-Z-but-2-ene-oate)-2-oxo-3S-phenylacetamido azetidine]disulfide, 4R,4'R bis[1-(tert-butyl 2-N-3-methyl-4-al-Z-but-2-ene-oate)-2-oxo-3S-phenoxyacetamido azetidine]disulfide, 4R,4'R bis[1-(p-methoxybenzyl 2-N-3-methyl-4-al-Z-but-2-ene-oate)-2-oxo-3S-(2-(p-methylphenyl-)acetamido)azetidine]disulfide, 4R,4'R bis[1-(benzyl 2-N-3-methyl-4-al-Z-but-2-ene-oate)-2-oxo-3S-(2-(p-methoxyphenyl-)acetamido)azetidine]disulfide, 4R,4'R bis[1-(tert-butyl 2-N-3-methyl-4-al-Z-but-2-ene-oate)-2-oxo-3S-(2-(4-benzylcarbonato-phenyl)acetamido azetidine]disulfide, 4R,4'R bis[1-(p-methoxybenzyl 2-N-3-methyl-4-al-Z-but-2-ene-oate)-2-oxa-3S-(4-chloro-phenylacetamido)azetidine]disulfide, 4R,4'R bis[1-(benzyl 2-N-3-methyl-4-al-Z-but-2-ene-oate)-2-oxo-3S-(2-chloro-phenylacetamido)azetidine]disulfide, 4R,4'R bis[1-(tert-butyl 2-N-3-methyl-4-al-Z-but-2-ene-oate)-2-oxo-3S-(4-trifluoromethyl-phenylacetamido)azetidine]disulfide, 4R,4'R bis[1-(benzyl 2-N-3-methyl-4-al-Z-but-2-ene-oate)-2-oxo-3S-(2-(4-benzyloxycarbonylphenyl-)acetamido)azetidine]disulfide, 4R,4'R bis[1-(tert-butyl 2-N-3-methyl-4-al-Z-but-2-ene-oate)-2-oxo-3S-(2-(4-benzylcarbonatomethylphenyl)acetamido)azetidine]disulfide, 4R,4'R bis[1-(p-methoxybenzyl 2-N-3-methyl-4-al-Z-but-2-ene-oate)-2-oxo-3S-(2-(4-benzyloxycarbonyl-methylphenyl)acetamido)azetidine]disulfide, 4R,4'R bis[1-(benzyl 2-N-3-methyl-4-al-Z-but-2-ene-oate)-2-oxo-3S-(2-(4-tert-butoxycarbonylaminomethylphenyl)acetamido)azetidine]disulfide, and 4R,4'R bis[1-(tert-butyl 2-N-3-methyl-4-al-Z-but-2-ene-oate)-2-oxo-3S-(2-(4-cyanophenyl-)acetamido)azetidine]disulfide.

The starting material utilized in the process of this invention is synthesized by first epimerizing the C-6 side chain of a penicillin sulfoxide from the β to the α conformation, followed by the rearrangement of the 6α-acylamino-penicillin sulfoxide to the corresponding 7α-acylamino-3-methyl cephalosporin. The final step in the synthesis of the starting material involves the 2α-alkoxylation of the above cephalosporin.

In this synthesis, the epimerization at the C-6 of the 6β-acylaminopenicillanate-1-sulfoxide to the 6α-acylaminopenicillanate-1-sulfoxide, represented by the following scheme:

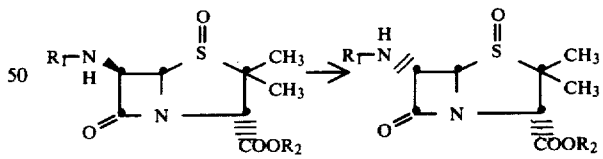

is a process well known to those skilled in the art. See, for example, Ramsay and Stoodley, *Chemical Communications,* 1971, 450, Koppel, *Tetrahedron Letters,* 1973, 4233, Stoodley, U.S. Pat. No. 3,853,848, Clair et al, J.C.S. *Perkin Transactions* I, 937 (1973), and Barton et al., J.C.S. *Perkin Transactions* I, 599, 1973. The preferred method of epimerization at the C-6 position involves reacting the naturally occurring 6β-acylamino compound with equimolar amount of chlorotrimethylsilane in methylene chloride at between 0° C. and ambient temperature, cooling the mixture to 0° C., and adding dropwise 2 moles of triethylamine per mole of penicillin sulfoxide substrate. The product can be purified by standard extraction and recrystallization techniques.

The desired α-isomer can be isolated by dissolving the isomer mixture from the reaction mixture in a minimum quantity of ethyl acetate and adding a few crystals of the β-isomer to facilitate crystallization of the β-isomer. The β-isomer crystals are filtered, resulting in a filtrate containing substantially pure (approximately 90%) α-isomer of the penicillanate, which α-isomer can be isolated by evaporating the filtrate to dryness.

The preferred procedure of C-6 epimerization is described by Blaszczak in copending application Ser. No. 138,022, entitled "Process for Penicillin Epimerization", filed this even date, now U.S. Pat. No. 4,320,055.

The rearrangement of 6α-acylaminopenicillinate-1-sulfoxide to the corresponding 7α-acylamino-3-methyl-3-cephem-4-carboxylate, represented by the following general formula,

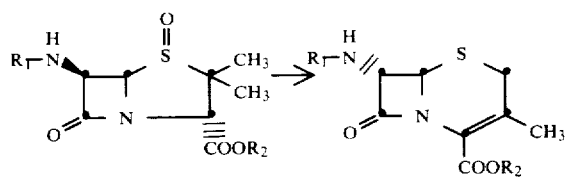

is analogous to a procedure also well known to those skilled in the art. Although several variations of the method are available to effect this rearrangement, the preferred method involves reacting the 6α-acylaminopenicillanate-1-sulfoxide with N,O-bis(trimethylsilyl)acetamide (BSA) and α-picoline.HBr in dried dioxane at reflux temperatures. The organic products of the reaction are then extracted into ethyl acetate, the ethyl acetate is evaporated, and the extract is treated with neat pyridine. Pure 7α-acylamino-3-methyl-3-cephem-4-carboxylate can be obtained by recrystallization.

The procedure for the above rearrangement step was adapted from one described by Verweij et al., in U.S. Pat. No. 4,003,894.

The last step in the above general reaction scheme involves an α-alkoxylation at the C-2 position of the cephem moiety, the product of this reaction being the starting material of the process of the invention in the present application. This reaction is represented in the following general formula,

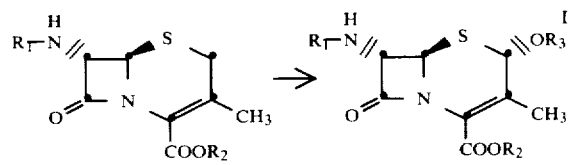

As with the above two steps in the synthesis of this starting material, the 2α-alkoxylation reaction involved at this stage of the synthesis is analogous to procedures well known to those skilled in the art; see, for example, D. O. Spry, *Tetrahedron Letters*, 3717 (1972); A. Yoshida, S. Oida, and E. Ohki, *Chemical and Pharmaceutical Bulletin of Japan* (Tokyo), 23, 2507 and 2518 (1975); ibid., 24 362 (1976); ibid., 25, 2082 (1977); C. O. Kim and P. A. McGregor, *Tetrahedron Letters*, 409 (1978). Although the aforementioned references describe various methods of 2α-alkoxylation for 7β-isomers of cephalosporins, the preferred method for the conversion of 7α-acylamino-3-methyl-3-cephem-4-carboxylate to its corresponding 2α-alkoxy analog comprises the addition of N-chlorosuccinimide to a solution of the substrate cephem compound dissolved in an appropriate alcohol and methylene chloride at room temperature. The desired 2α-alkoxy product can then be isolated by standard crystallization and chromatography techniques.

The compounds of this invention are intermediates useful in the preparation of a particular class of biologically active 1-oxa β-lactam compounds. The conversion of the symmetrical azetidinone aldehyde disulfide compounds to 3-methyl 1-oxa β-lactam antibiotics is accomplished by first reducing the symmetrical azetidinone aldehyde disulfide compounds to the corresponding alcohol compounds, followed by the cyclization of these alcohols to 7α-acylamino 1-oxa β-lactam compounds. These 1-oxa β-lactam compounds are then 7α-methoxylated, followed by removal of the protecting group of the carboxylic acid function at C-4 to give the desired 7β-acylamino-7α-methoxy 1-oxa β-lactam antibiotic compounds.

As mentioned above, the first step of the synthesis of the desired antibiotic 1-oxa β-lactam compound involves reducing the symmetrical azetidinone aldehyde disulfide compounds, the compounds claimed in this application, with sodium cyanoborohydride to give the corresponding alcohols. This reaction is represented by the general formula,

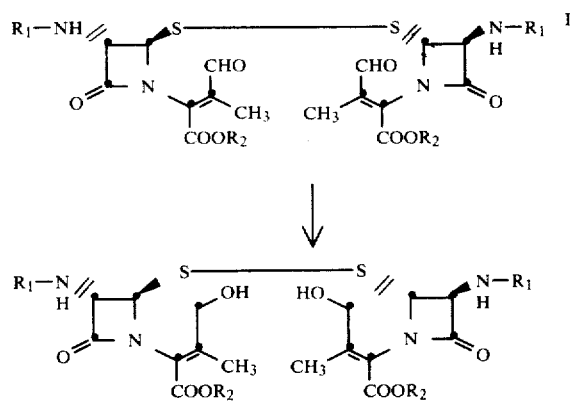

The procedure for this reduction is outlined generally in R. F. Borch, M. D. Bernstein, and H. D. Durat, *Journal of the American Chemical Society*, 93, 2897 (1971) and consists of dissolving the aldehyde compound in aqueous tetrahydrofuran, acidifying the mixture, and then adding the sodium cyanoborohydride reducing agent. The desired alcohol can be purified by conventional extraction techniques.

The symmetrical azetidinone alcohol disulfide compounds are subsequently cyclized to give a 7α-acylamido-3-methyl 1-oxa β-lactam represented by the following general formula,

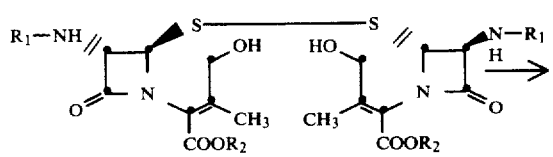

-continued

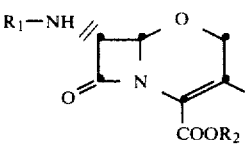  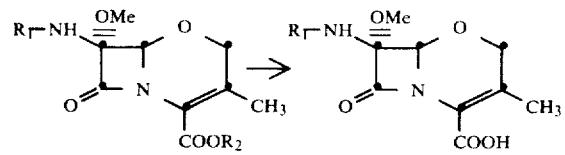

This cyclization is accomplished by reacting the alcohol compounds with a cyclization reagent selected from the group consisting of divalent mercury salts or phosphines. The divalent mercury salts are of the general formula Hg(X)$_2$, where X is chloro, bromo or trifluoroacetato. The mercury cyclization reagent and the substrate alcohol compound are reacted in a dry, polar, inert organic solvent such as acetonitrile. The phosphine cyclization reagent compounds have the general formula

wherein R$_4$ can be alkyl, for example, methyl or ethyl, phenyl or substituted phenyl, for example, 4-methylphenyl. The phosphorus reagent and the substrate alcohol are reacted in a dry, inert, organic solvent such as 1,2-dichloroethane. The desired cyclized product obtained by the use of either class of cyclizing reagent can be purified by conventional chromatographic techniques.

The cyclization of the symmetrical azetidinone alcohol disulfide compounds to the corresponding 7α-acylamino-3-methyl 1-oxa β-lactam antibiotic is described by Kukolja and Pfeil in copending application Ser. No. 137,862, entitled "Azetidinone Alcohol Disulfide and Process for Cyclization" filed this even date, now U.S. Pat. No. 4,293,493.

The 7α-acylamino-3-methyl 1-oxa β-lactam ester compounds are then converted to the 7β-acylamino-7α-methoxy-3-methyl 1-oxa β-lactam esters by reacting the 7α-acylamino substrate with lithium methoxide and tert-butyl hypochlorite. This reaction is represented generally by the following formula,

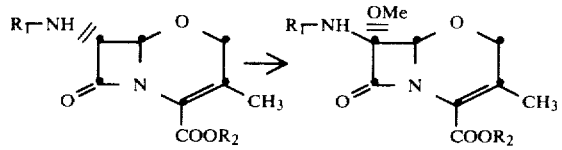

The reaction entails the addition of the 7α-acylamino 1-oxa β-lactam to a suspension of lithium methoxide in dry tetrahydrofuran in an inert atmosphere followed by addition of tert-butyl hypochlorite to the solution to initiate the methoxylation. Once the reaction has reached completion, the reaction is quenched with trimethylphosphite and glacial acetic acid. The desired product can be isolated and purified with conventional liquid-liquid extraction techniques.

The above methoxylation of the 7α-acylamino-3-methyl 1-oxa β-lactam is carried out in a matter analogous to that of G. A. Koppel and R. E. Koehler, *Journal of the American Chemical Society*, 95, 2403 (1973).

The final step in the synthesis of a 1-oxa β-lactam compounds from the claimed symmetrical azetidinone aldehyde disulfide compounds is to remove the carboxylic acid protecting group from the 7β-acylamino-7α-methoxy-3-methyl 1-oxa β-lactam ester compound, as represented by this general formula, The deprotection step is well known to anyone skilled in the art. For example, to remove the diphenylmethyl carboxylic acid protecting group, the substrate diphenylmethyl carboxylate is dissolved in anisole and is then treated with trifluoroacetic acid. The resultant 7β-acylamino-7α-methoxy-3-methyl 1-oxa β-lactam acid is one example of a 1-oxa β-lactam antibiotic compound. Further examples of the deprotection step can be found in U.S. Pat. No. 4,138,486.

The following Examples (1-3) are provided to further illustrate this invention. Preparations 1 through 3 demonstrate a method of synthesizing the starting materials for the process of the invention, and preparations 4-8 demonstrate a method of converting the claimed compounds of this invention into biologically active 1-oxa β-lactam compounds. It is not intended that this invention be limited in scope by reason of any of the preparations or examples. In the following preparations and examples infrared absorption spectra, nuclear magnetic resonance spectra, ultraviolet absorption spectra and optical rotation spectra are abbreviated i.r., n.m.r., u.v. and o.r., respectively. Only the i.r. absorption maxima attributable to the carbonyl function of the β-lactam ring are reported. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed as Hz.

EXAMPLE 1

4R,4′R bis[1-(benzyl 2-N-3-methyl-4-al-Z-but-2-ene-oate)-2-oxo-3S-phenylacetamido azetidine]disulfide.

To a solution of benzyl 7-(2-phenylacetamido)-2α-methoxy-3-methyl-3-cephem-4-carboxylate (1.6 g, 3.5 mmol) in 50 ml of methylene chloride at 0° C. was added N-chlorosuccinimide (0.49 g, 3.64 mmol). The solution was stirred for 15 minutes, and was added to a rapidly stirring suspension of mercury dichloride (2.9 g, 10.6 mmol) and cadmium carbonate (3.78 g, 22 mmol) in 50 ml of water. The mixture was stirred at ambient temperature for 30 min., and filtered through prewashed Celite. The methylene chloride layer was then separated and evaporated to dryness. The product was taken up in ethyl acetate and the ethyl acetate solution was washed with water (5X) then with saturated sodium chloride solution (1X) and subsequently dried over magnesium sulfate. Filtration and evaporation to dryness gave crude product (1.5 g, 99% yield) of which 400 mg was chromatographed on 15 grams of silica gel using 1:1 ethyl acetate:hexane as the eluant. The product, 4R,4′R bis[1-(benzyl 2-N-3-methyl-4-al-Z-but-2-ene-oate)-2-oxo-3S-phenylacetamido azetidine]disulfide was isolated as a yellow foam (247 mg, 62% yield): i.r. (CHCl$_3$) 1785 cm$^{-1}$ (β-lactam C=O); u.v. λ$_{max}$ (CHCl$_3$)=291 nm, (ε=14,567); n.m.r. (CDCl$_3$) δ 2.00 (s, 3, CH$_3$), 3.52 (s, 2, CH$_2$Ph), 4.90 (dd, J=2 and 8 Hz, 1, C$_3$—H), 5.20 (br. s, 2, CO$_2$CH$_2$Ph), 5.33 (d, J=2 Hz, 1, C4—H), 7.25 (s, 10, aromatic H), 7.60 (d, J=8 Hz, 1, N—H), and 9.80 (s, 1, CHO).

Analysis: Calculated for C58H50N4O10S2: C, 63.14; H, 4.84; N, 6.40; O, 18.28; S, 7.33; Found: C, 63.21; H, 4.97; N, 6.16; O, 18.40; S, 7.08.

EXAMPLE 2

4R,4R bis[1-(tert-butyl 2-N-3-methyl-4-al-Z-but-2-ene-oate)-2-oxo-3S-(2-isobutoxycarbonylamino-2-phenylacetamido azetidene]disulfide.

To the tert-butyl 7α-(2-isobutoxycarbonylamino-2-phenylacetamido)-2α-methoxy-3-methyl-3-cephem-4-carboxylate in methylene chloride at 0° C. is added N-chlorosuccinimide. This solution is stirred for 15 minutes, then is added to a rapidly stirring suspension of mercury dichloride and cadmium carbonate in water. The resultant reaction mixture is stirred at ambient temperature for 30 minutes and filtered through pre-washed Celite. The methylene chloride is then separated and evaporated to dryness. The product is taken up in ethyl acetate and the ethyl acetate solution is washed with water (5X) then with saturated sodium chloride solution (1X) and is subsequently dried over magnesium sulfate. Filtration and evaporation to dryness gives crude product which is chromatographed on silica gel using 1:1 ethyl acetate:hexane as the eluant.

EXAMPLE 3

4R,4'R bis[1-(p-methoxybenzyl 2-N-3-methyl-4-al-Z-but-2-ene-oate)-2-oxo-3S-phenoxyacetamido azetidine]-disulfide.

To the 4-methoxybenzyl 7-(2-phenoxyacetamido)-2α-methoxy-3-methyl-3-cephem-4-carboxylate in methylene chloride at 0° is added N-chlorosuccinimide. The solution is stirred for 15 minutes, then is added to a rapidly stirring suspension of mercury dichloride and cadmium carbonate in water. The mixture is stirred at ambient temperature for 30 min., and is filtered through pre-washed Celite. The methylene chloride is then separated and evaporated to dryness. The product is taken up in ethyl acetate and the ethyl acetate solution is washed with water (5X) then with saturated sodium chloride solution (1X) and subsequently dried over magnesium sulfate. Filtration and evaporation to dryness gives crude product which is chromatographed on silica gel using 1:1 ethyl acetate:hexane as the eluant.

Preparation 1

Benzyl 6α-phenylacetamidopenicillanate-1-sulfoxide.

Benzyl 6β-phenylacetamidopenicillanate-1-sulfoxide (8.80 g, 20 mmol) was dissolved in 17 ml of methylene chloride under a positive nitrogen pressure, and the resultant solution was cooled to 2° C. in an ice/water bath. Triethylamine (6.1 ml, 43.8 mmol) was added to the cooled solution, which resulted in the precipitation of the penicillanate. Thirteen more ml of methylene chloride was added to the solution to dissolve the penicillanate, followed by the addition of chlorotrimethylsilane (2.8 ml, 22 mmol). The reaction solution was stirred for 1 hour at 0° C., allowed to warm to ambient temperature and stirred for 1.5 hours longer, at the end of which time more chlorotrimethylsilane (1 ml, 7.86 mmol) was added and the stirring was continued for an additional 45 minutes. After cooling the reaction mixture to 4° C., acetic acid (3 ml, 52 mmol) was added dropwise, followed by addition of methylene chloride (20 ml). The reaction solution was then washed with 1 molar hydrochloric acid (3X) and with a saturated sodium bicarbonate solution (2X). The layers were separated, and the water layer was extracted with methylene chloride (1X). The methylene chloride layers were combined, washed with a saturated sodium chloride solution (1X) then dried over magnesium sulfate, filtered and evaporated to dryness. The resultant off-white foam (8.3 g) was recrystallized from a 1:1 mixture of ethyl acetate/cyclohexane. Five grams of the crystallized product was dissolved in 13 ml of ethyl acetate, and seeded with benzyl 6β-phenylacetamido penicillanate-sulfoxide crystals, to yield white crystals of the β-isomer of the penicillanate (760 mg). The crystals of the β-isomer of the pencillanate of benzyl 6-phenylacetamidopenicillanate-1-sulfoxide were filtered off and the filtrate yielded predominately pure (90%) α-isomer of benzyl 6-phenylacetamidopenicillanate-1-sulfoxide (4.06 g, 46% yield). n.m.r. (d5-pyridine) δ1.13, 1.62 (s, 6, C(CH3)2), 3.78 (s, 2, COCH2Ph), 4.92 (s, 1, C3—H), 5.22 (br. s, 2, CO2CH2Ph), 5.52 (d, J=2 Hz, 1, C5—H), 5.88 (dd, J=2 and 8 Hz, 1, C6—H), 7.33 (m, 10, aromatic), 10.13 (d, J=8 Hz, 1, NH).

Preparation 2

Benzyl 7α-phenylacetamido-3-methyl-3-cephem-4-carboxylate.

To a solution of benzyl 6α-phenylacetamidopenicillanate-1-sulfoxide (31.4 g, 71.6 mmol) in dried dioxane (500 ml) was added N,O-bis(trimethylsilyl) acetamide (BSA) (39 ml, 158 mmol) and 58 ml of an α-picoline.HBr solution (1.23 M in CH2Cl2, 71.6 mmol). This reaction mixture was refluxed for 5 hours, during which time the reaction solution color changed from yellow to brown. The reaction solution was cooled to ambient temperature and poured into a stirred mixture of 1:1 ethyl acetate/ice water. The layers were separated and the ethyl acetate layer was washed sequentially with saturated sodium chloride solution (1X), 1 molar hydrochloric acid (4X), saturated sodium bicarbonate solution (1X), and again with saturated sodium chloride solution (2X). The ethyl acetate layer was then dried over magnesium sulfate, filtered, evaporated to dryness, and treated with neat pyridine (10 ml, 0.12 mole) for 1 hour. The pyridine solution was taken up in methylene chloride and washed first with 1 molar hydrochloric acid several times, then with brine solution (1X). The extract was dried over magnesium sulfate, filtered and evaporated to dryness. The resultant crude product was recrystallized by dissolution in a (7:1) ethyl acetate:cyclohexane solution and addition of a few seed crystals of the title product. Two crops of crystals were collected and gave a combined yield of 8.70 grams (29% yield) of substantially pure 7α-phenylacetamido-3-methyl-3-cephem-4-carboxylate (m.p. 169°-170° C.); i.r. (CHCl3) 1773 cm−1; n.m.r. (CDCl3) δ2.00 (s, 3, CH3), 3.10, 3.37 (ABq, J=15 Hz, 2, C2—H), 3.53 (s, 2, COCH2Ph), 4.55 (d, J=2 Hz, 1, C6—H), 4.85 (dd, J=2 and 8 Hz, 1, C7—H), 5.10 (s, 2, CO2CH2Ph), 6.98 (d, J=8 Hz, 1, NH), 7.27 (s, 5, aromatic protons); 7.35 (s, 5, aromatic protons) u.v. (CHCl3) λmax 264 nm (ε=8,210), o.r. [α]D25° +46.9°; mass spectrum, m/e 422.

Analysis: Calculated for C23H22N2O3S: C, 65.38; H, 5.25; N, 6.63; O, 15.15; S, 7.59. Found: C, 65.25; H, 5.09; N, 6.63; O, 14.88; S, 7.44.

Preparation 3

Diphenylmethyl 7α-phenylacetamido-2α-methoxy-3-methyl-3-cephem-4-carboxylate.

To a solution of diphenylmethyl 7α-phenylacetamido-3-methyl-3-cephem-4-carboxylate (2.88 g, 5.8 mmole) in 40 ml of methanol and 60 ml of methylene chloride, was added N-chlorosuccinimide (882 mg, 6.6 mmol) and the mixture was stirred for 90 minutes at room temperature. The reaction solution was then washed with brine (2X) and dried over magnesium sulfate, filtered and the solvent was evaporated under reduced pressure. The resultant yellow foam (2.84 g) was chromatographed over 100 grams of silica gel employing 10-15% of ethyl acetate in toluene as the eluting solvent. The first fraction to elute from the column was the desired 2α-methoxy cephem compound which was subsequently recrystallized from a mixture of ethyl acetate and cyclohexane to give pure diphenylmethyl 7α-phenylacetamido-2α-methoxy-3-methyl-3-cephem-4-carboxylate. (638 mg, 21% yield) (m.p. 144°-145° C.) i.r. (CHCl$_3$) 1780, 1725 and 1680 cm$^{-1}$; n.m.r. (CDCl$_3$) δ1.95 (s, 3, CH$_3$) 3.35 (s, 3, OCH$_3$), 3.45 (s, 2, CH$_2$Ph), 4.60 (s, 1, C$_2$—H), 4.70 (d, J=2 and 8 Hz, 1, C$_7$—H), 4.85 (d, J=2 Hz, 1, C$_6$—H), 6.95 (s, 1, CH$_2$Ph), 7.3 (m, 16, aromatic H and N-H); u.v. (CHCl$_3$) λ$_{max}$ 264 nm (ε=9726).

Analysis: Calculated for C$_{30}$H$_{28}$N$_2$O$_5$S: C, 68.16; H, 5.34; N, 5.30; S, 6.07. Found: C, 68.36; H, 5.33; N, 5.29; S, 5.90.

Preparation 4

4R,4'R bis[1-(diphenylmethyl 2-N-3-methyl-4-ol-Z-but-2-ene-oate)-2-oxo-3S-phenylacetamido azetidine]disulfide.

4R,4'R bis[1-(diphenylmethyl 2-N-3-methyl-4-al-Z-but-2-ene-oate)-2-oxo-3S-phenylacetamido azetidine]disulfide (524 mg, 0.51 mmol) was dissolved in a solution of 10 ml tetrahydrofuran (THF) and 1 ml of water. The pH of this solution was adjusted to 3.5 with a 1 molar THF solution of sodium hyroxide. Sodium cyanoborohydride (63 mg, 1.0 mmol) was added to the solution and the reaction mixture was stirred at room temperature for 0.5 hour during which time the pH of the solution was maintained between 3.2 and 3.6 with additions of a solution of 3 ml of 1 molar hydrochloric acid and 3 ml of acetic acid in 20 ml of THF. At the end of 0.5 hour, the reaction solution was poured into a solution composed of 75 ml of saturated sodium chloride solution and 50 ml of ethyl acetate, and the resultant solution was stirred for ten minutes. The layers were then separated and the ethyl acetate layer was washed sequentially with water (1X), saturated sodium bicarbonate (1X), water (1X), saturated sodium chloride (1X), and was then dried over magnesium sulfate, filtered and evaporated to dryness. The resulting colorless foam was the product, 4R,4'R bis[1-(diphenylmethyl 2-N-3-methyl-4-ol-Z-but-2-ene-oate)-2-oxo-3S-phenylacetamido azetidine]disulfide (500 mg): n.m.r. (CDCl$_3$) δ2.18 (s, 3, CH$_3$), 3.48 (s, 2, CH$_2$Ph), 3.93 and 4.20 (ABq, J=13 Hz, 2, CH$_2$OH), 4.87 (dd, J=2 and 9 Hz, 1, C$_3$—H), 5.04 (d, J=2 Hz, 1, C$_4$—H), 6.86 (s, 1, CH$_2$Ph), and 7.28 (br, s, 16, aromatic H and N—H).

Preparation 5

7α-Phenylacetamido-3-methyl 1-oxa β-lactam diphenylmethyl ester.

Bis(trifluoroacetato)mercury (II) (1.48 g, 3.4 mmol) and 4R,4'R bis[1-(diphenylmethyl 2-N-3-methyl-4-ol-Z-but-2-ene-oate)-2-oxo-3S-phenylacetamido azetidine]disulfide (866 mg, 0.84 mmol) were dissolved under positive pressure of nitrogen in 16 ml. of dried acetonitrile. The reaction mixture was stirred for 0.5 hour at ambient temperature, at the end of which time it was filtered and the filtrate was taken to dryness. The resulting orange foam was dissolved in ethyl acetate and the ethyl acetate solution was washed with water (1X), saturated sodium chloride solution (1X), and then with a sodium chloride solution until the wash water was neutral. The ethyl acetate layer was filtered through a sintered glass funnel, dried over magnesium sulfate, filtered, and evaporated to dryness, yielding a dark orange foam (773 mg). This foam was recrystallized from an acetone/cyclohexane mixture and subsequent filtration of this mixture isolated pure crystals of the desired product, 7α-phenylacetamido-3-methyl 1-oxa β-lactam diphenylmethyl ester (65 mg). The filtrate from the above recrystallization was combined with the filtrate from another experiment done analogous to the instant one, and this combined filtrate was chromatographed on silica gel eluting with 20% ethyl acetate in toluene to give more of the desired 7α-phenylacetamido-3-methyl 1-oxa β-lactam diphenylmethyl ester (m.p. 190°-191°), i.r. (CHCl$_3$) 1780 cm$^{-1}$; n.m.r. (d$_6$-acetone) δ1.93 (s, 3, CH$_3$), 3.6 (s, 2, CH$_2$Ph), 4.35 (br, s, 2, C$_2$13 H), 4.73 (dd, J=1.5 and 9 Hz, 1, C$_7$—H), 4.99 (d, J=1.5 Hz, 1, C$_6$—H), 6.89 (s, 1, CH$_2$Ph), and 7.3 (m, 16, aromatic H and N-H); mass spectrum, m/e 406; u.v. λ$_{max}$ 263 nm (ε=6,072).

Preparation 6

7α-Phenylacetamido-3-methyl 1-oxa β-lactam diphenylmethyl ester.

Triphenylphosphine (278 mg, 1.06 mmol) and 4R,4'R bis[1-(diphenylmethyl 2-N-3-methyl-4-ol-Z-but-2-ene-oate)-2-oxo-3S-phenylacetamido azetidine]-disulfide (464 mg, 0.52 mmol) were combined in 10 ml of dry 1,2-dichloroethane. The solution was refluxed for seventy minutes, after which time it was evaporated to dryness. The resulting yellow oil was chromatographed on 15 grams of silica gel using 1:1 ethyl acetate/hexane plus ½% acetic acid as the eluant. The pure product, 7α-phenylacetamido-3-methyl 1-oxa β-lactam diphenylmethyl ester (67 mg), possessed the same physical properties as the product compound in Preparation 5.

Preparation 7

7β-Phenylacetamido-7α-methoxy-3-methyl 1-oxa β-lactam diphenylmethyl ester.

Phenylacetamido-3-methyl 1-oxa β-lactam diphenylmethyl ester (121 mg, 0.25 mmol) was added to a suspension of lithium methoxide in 5 ml of dry THF (made by adding 1 ml dry methanol to 5.8 mg, 0.83 mmol of lithium in THF) under positive N$_2$ pressure at −70° C. tert-Butyl hypochlorite (0.0356 ml, 0.315 mmol) was added to this solution which was then stirred for 30 minutes at −70° C., at the end of which time trimethylphosphite (0.0075 ml) and then glacial acetic acid (0.0625 ml) were added to the solution to quench the reaction. The reaction mixture was allowed to warm to ambient temperature, evaporated to dryness, and the residue was dissolved in ethyl acetate/water solution and washed sequentially with 1 molar hydrochloric acid solution brine (1X), 5% sodium bicarbonate solution (1X), water (1X), and brine (1X). The washed solution was dried over magnesium sulfate, filtered and then evaporated to dryness to give a white foam of the product, 7β-phenylacetamido-7α-methoxy-3-methyl 1-oxa β-lactam diphenylmethyl ester (123 mg). Recrystallization from acetone gave white crystals, (mp.

187°–187.5°C.): i.r. (CHCl$_3$) 1780 cm$^{-1}$; n.m.r. (d$_6$-acetone) δ1.99 (s, 3, CH$_3$), 3.46 (s, 3, OCH$_3$), 3.68 (s, 2, CH$_2$Ph), 4.34 (br, s, 2, C$_2$—H), 5.05 (s, 1, C$_6$—H), 6.91 (s, 1, CHPh$_2$), and 7.3 (m, 16, aromatic H and N—H); mass spectrum, m/e 512.

Preparation 8

7β-Phenylacetamido-7α-methoxy-3-methyl 1-oxa β-lactam acid.

7β-Phenylacetamido-7α-methoxy 1-oxa β-lactam diphenylmethyl ester (50 mg., 0.01 mmol) was dissolved in 0.1 ml of anisole, cooled to 0° C., and trifluoroacetic acid (0.4 ml) was slowly added to the reaction mixture. The reaction mixture was stirred for 10 minutes at 0° C., diluted with ethyl acetate, evaporated at ambient temperature, and the resulting colorless oil was taken up in 20 ml of ethyl acetate at 0° C. Ten ml of water at 0° C. was added to the ethyl acetate solution, the resulting slurry's pH was adjusted to pH 8 with 0.04 molar sodium hydroxide solution and the layers were then separated. Ten ml of ethyl acetate at 0° C. was added to the water layer, and the resulting slurry's pH was adjusted to pH 3.0 (at 0° C.) with 0.04 molar hydrochloric acid. The layers were separated, and the ethyl acetate layer was washed with saturated sodium chloride solution (1X), dried over magnesium sulfate and evaporated to dryness. The crude product was recrystallized from acetone to give pure 7β-phenylacetamido-7α-methoxy-3-methyl 1-oxa β-lactam acid (20 mg, 59% yield) (m.p. 169°–170°C.): i.r. (KBr) 1782 cm$^{-1}$; n.m.r. (d$_6$-acetone) δ2.00 (s, 3, CH$_3$), 3.43 (s, 3, OCH$_3$), 3.53 (s, 2, CH$_2$Ph), 4.39 (br, s, 2, C$_2$—H), 5.07 (s, 1, C$_6$—H), 5.70 (br, s, 1, COOH), 7.33 (s, 5, aromatic H), and 7.95 (s, 1, N—H).

We claim:

1. A process for preparing symmetrical azetidinone aldehyde disulfide compounds of the formula

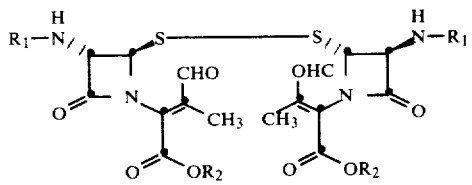

which comprises:
(1) reacting a 2α-alkoxy cephalosporin ester of the formula

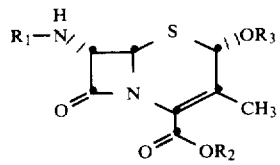

with about 1 to about 1.3 equivalents of an N-chloro halogenating agent in a chlorinated hydrocarbon solvent at a temperature between −10° C. and 30° C.;

(2) combining the above solution with an aqueous suspension of between about 2 and about 4 molar equivalents of mercury dichloride and about 5 to about 7 molar equivalents of cadmium carbonate at a temperature between about 0° C. and about 30° C.; where in the above formulae R$_1$ is an acyl group of the formula

wherein R' is
(a) C$_1$–C$_7$ alkyl, cyanomethyl, C$_1$–C$_6$ haloalkyl, 4-protected amino-4-protected carboxybutyl; or
(b) C$_1$–C$_6$ alkoxy, phenoxy, benzyloxy or p-methoxybenzyloxy; or
(c) the group —R" wherein R" is phenyl or substituted phenyl wherein the substituents are 1 or 2 halogens, protected hydroxy, cyano, trifluoromethyl, C$_1$–C$_4$ alkyl, C$_1$–C$_4$ alkoxy, protected carboxy, protected carboxymethyl, protected hydroxymethyl or protected aminomethyl; or
(d) an arylalkyl group of the formula

wherein m is 0 or 2; or
(e) a substituted arylalkyl group of the formula

wherein R''' is R" as defined above, 2-thienyl, 3-thienyl, 2-furyl or 3-furyl; W is protected hydroxy, protected carboxy, protected amino, or
(f) a heteroarylmethyl group of the formula

wherein R'''' is 2-thienyl, 3-thienyl, 2-furyl, 3-furyl, 2-thiazolyl, 5-tetrazolyl, 1-tetrazolyl;

R$_2$ is a carboxy protecting group; and R$_3$ is methyl, ethyl or isopropyl.

2. The process of claim 1 wherein R$_2$ is benzyl, diphenylmethyl, tert-butyl, p-methoxybenzyl, 2,4,6-trimethylbenzyl, trityl, 4-methoxytrityl, 4,4'-dimethoxytrityl, or 4,4',4"-trimethoxytrityl.

3. The process of claim 1 wherein R$_1$ is an acyl group of the formula

wherein R' is
(a) C$_1$–C$_7$ alkyl, cyanomethyl;
(b) C$_1$–C$_6$ alkoxy;
(c) benzyl, 1-phenoxymethyl, 1-p-methoxyphenylmethyl;
(d) 2-thienylmethyl, 3-thienylmethyl, 2-furylmethyl, 3-furylmethyl, 2-thiazolylmethyl 5-tetrazolylmethyl;
(e) 1-protected hydroxy-1-phenylmethyl, 1-protected amino-1-phenylmethyl, 1-protected amino-1-(4-protected hydroxyphenyl)methyl.

4. The process of claim 3 wherein R$_2$ is benzyl, diphenylmethyl, tert-butyl, p-methoxybenzyl, 2,4,6-trimethylbenzyl, trityl, 4-methoxytrityl, 4,4'-dimethoxytrityl, or 4,4',4"-trimethoxytrityl.

5. The process of claim 4 wherein R$_2$ is benzyl.

6. The process of claim 1 wherein R$_1$ is an arylalkyl group of the formula

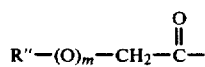

wherein R" is phenyl or substituted phenyl wherein the substituents are 1-2 halogens, protected hydroxy, cyano, trifluoromethyl, $C_1$-$C_4$ alkyl, $C_1$-$C_4$ alkoxy, protected carboxy, protected carboxymethyl, protected hydroxymethyl or protected aminomethyl; and m is 0 or 1.

7. The process of claim 6 wherein $R_2$ is benzyl, diphenylmethyl, tert-butyl, p-methoxybenzyl, 2,4,6-trimethylbenzl, trityl, 4-methoxytrityl, 4,4'-dimethoxytrityl, 4,4',4''-trimethoxytrityl.

8. The process of claim 7 wherein $R_1$ is benzyl.

9. The process of claim 8 wherein $R_2$ is benzyl.

10. The process of claim 1 wherein $R_3$ is methyl.

11. The process of claims 1, 3 or 6 in which the N-chloro halogenating agent is a compound of the formula

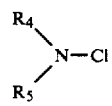

in which $R_4$ is hydrogen, chloro, $C_1$-$C_3$ alkyl, cyclohexyl, phenyl, or phenyl substituted with chloro, bromo, methyl, or nitro, and $R_5$ is $R_6$—X— in which $R_6$ is $C_1$-$C_3$ alkyl, cyclohexyl, phenyl, or phenyl substituted with chloro, bromo, methyl, or nitro, and X is

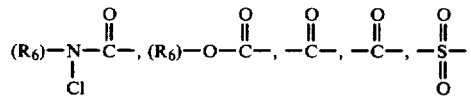

or —$SO_2$—; or $R_4$ and $R_5$ taken together with the nitrogen to which they are bonded define a heterocyclic structure of the formula

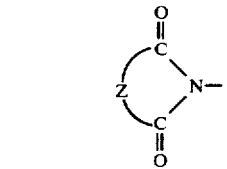

in which Y is o-phenylene, or —$(CH_2)_n$— in which n is 2 or 3; or a structure of the formula

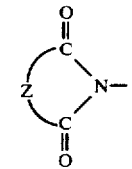

in which Z is Y as hereinbefore defined or a group of the formula

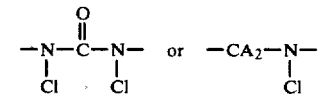

in which A is hydrogen or methyl.

12. The process of claim 11, in which the N-chloro halogenating agent has the formula

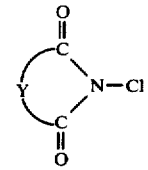

in which Y is o-phenylene or —$CH_2$—$CH_2$—.

13. The process of claim 12, in which the N-chloro halogenating agent is N-chlorosuccinimide.

14. The process of claim 9 wherein the N-chloro halogenating agent has the formula

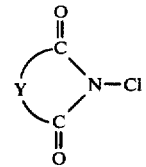

in which Y is o-phenylene or —$CH_2$—$CH_2$—.

15. The process of claim 14 in which the N-chloro halogenating agent is N-chlorosuccinimide.

* * * * *